US012589211B2

(12) United States Patent
Berler et al.

(10) Patent No.: US 12,589,211 B2
(45) Date of Patent: Mar. 31, 2026

(54) NEEDLE AND SYRINGE SYSTEM WITH AUTOMATIC SAFETY SHIELD THAT RENDERS A NEEDLE SAFE

(71) Applicant: Sharps Technology, Inc., Melville, NY (US)

(72) Inventors: Barry B. Berler, Huntingdon Valley, PA (US); Uzi Malimovka, Givat-Shmuel (IL)

(73) Assignee: Plasto Technology Group LLC, Huntington Valley, PA (US)

( * ) Notice: Subject to any disclaimer, the term of this patent is extended or adjusted under 35 U.S.C. 154(b) by 971 days.

(21) Appl. No.: 17/581,914

(22) Filed: Jan. 22, 2022

(65) Prior Publication Data

US 2022/0241517 A1 Aug. 4, 2022

Related U.S. Application Data

(60) Provisional application No. 63/143,700, filed on Jan. 29, 2021.

(51) Int. Cl.
*A61M 5/32* (2006.01)
(52) U.S. Cl.
CPC .......... *A61M 5/326* (2013.01); *A61M 5/3216* (2013.01); *A61M 5/3234* (2013.01); *A61M 5/3245* (2013.01); *A61M 2005/3268* (2013.01)
(58) Field of Classification Search
CPC ........ A61M 5/3275; A61M 2005/3267; A61M 2005/3268; A61M 2005/3269; A61M 2005/3271; A61M 2005/3258; A61M 25/0631; A61M 2005/3261; A61M 2005/3263; A61M 5/3269; A61M 5/3271
See application file for complete search history.

(56) References Cited

U.S. PATENT DOCUMENTS

| 4,559,043 | A | 12/1985 | Whitehouse et al. |
| 4,986,813 | A | 1/1991 | Blake, III et al. |
| 5,104,384 | A | 4/1992 | Parry |
| 5,205,826 | A | 4/1993 | Chen |
| 5,306,258 | A | 4/1994 | de la Fuente |

(Continued)

FOREIGN PATENT DOCUMENTS

| CA | 2236049 | 7/2006 |
| EP | 1 645 302 | 2/2007 |

(Continued)

*Primary Examiner* — Chelsea E Stinson
*Assistant Examiner* — Nelson Louis Alvarado, Jr.
(74) *Attorney, Agent, or Firm* — LaMorte & Associates P.C.

(57) ABSTRACT

A safety syringe system that automatically shields a needle after an injection. A plunger extends into a barrel. An elastic return construct is provided that has at least one stretchable arm. The elastic return construct engages the barrel and positions each stretchable arm along the exterior of the barrel. A safety shield is provided that slides over a first end of the barrel. In a first position, the needle is protected by the safety shield. In a second position, the needle is exposed. The safety shield engages and stretches the elastic return construct when moved from the first position to the second position. A locking mechanism is used to lock the safety shield into its second position. The locking mechanism is released by elements displaced by movement of the plunger.

20 Claims, 10 Drawing Sheets

(56) References Cited

U.S. PATENT DOCUMENTS

| | | | |
|---|---|---|---|
| 5,314,503 | A | 5/1994 | Bobrove et al. |
| 5,370,628 | A | 12/1994 | Allison et al. |
| 5,385,555 | A | 1/1995 | Hausser |
| 5,460,611 | A | 10/1995 | Alexander |
| 5,531,696 | A | 7/1996 | Menes |
| 5,733,264 | A | 3/1998 | Flowers |
| 5,891,092 | A | 4/1999 | Castellano |
| 5,902,270 | A | 5/1999 | Jentzen |
| 6,186,980 | B1 | 2/2001 | Brunel |
| 6,613,022 | B1 * | 9/2003 | Doyle .................... A61M 5/326 604/192 |
| 6,616,636 | B2 | 9/2003 | Lee |
| 6,626,863 | B1 | 9/2003 | Berler |
| 7,527,607 | B2 | 5/2009 | Botich |
| 7,604,613 | B2 | 10/2009 | Crawford et al. |
| 8,821,453 | B2 * | 9/2014 | Doyle .................... A61M 5/326 604/263 |
| 9,757,520 | B2 | 9/2017 | Corrigan |
| 2003/0130623 | A1 | 7/2003 | Chen |
| 2004/0162530 | A1 | 8/2004 | Kirk |
| 2007/0016140 | A1 | 1/2007 | Berler |
| 2007/0016145 | A1 | 1/2007 | Berler |
| 2008/0009808 | A1 | 1/2008 | Berler |
| 2008/0097337 | A1 | 4/2008 | Judd et al. |
| 2008/0319346 | A1 | 12/2008 | Crawford et al. |
| 2010/0076378 | A1 | 3/2010 | Runfola |
| 2011/0257603 | A1 | 10/2011 | Ruan et al. |
| 2016/0045676 | A1 | 2/2016 | Klippenstein |
| 2016/0279333 | A1 | 9/2016 | Russo et al. |
| 2016/0279344 | A1 | 9/2016 | Shluzas et al. |
| 2016/0367764 | A1 | 12/2016 | Doyle |
| 2017/0319791 | A1 | 11/2017 | Giambattista et al. |

FOREIGN PATENT DOCUMENTS

| | | |
|---|---|---|
| EP | 1 495 776 | 12/2008 |
| WO | WO 91/12841 | 9/1991 |
| WO | WO 2004/035120 | 4/2004 |
| WO | WO 2006/008086 | 1/2006 |

* cited by examiner

NEEDLE AND SYRINGE SYSTEM WITH AUTOMATIC SAFETY SHIELD THAT RENDERS A NEEDLE SAFE

RELATED APPLICATIONS

This application claims the benefit of U.S. provisional application No. 63/143,700 filed Jan. 29, 2021.

BACKGROUND OF THE INVENTION

1. Field of the Invention

In general, the present invention relates to syringes that are used to make injections through a needle or cannula. More particularly, the present invention relates to safety syringes with a spring-loaded shield, wherein the needle automatically becomes shielded after use.

2. Prior Art Description

Millions of injections are performed globally each year. The injections are typically performed using a hypodermic needle and a syringe. The length of the hypodermic needle and the gauge of the needle depend upon the application and whether the injection is intramuscular, subcutaneous, intravenous, or intradermal.

Safety syringe assemblies are designed to both perform. an. injection and to provide some mechanism for minimizing the likelihood of a needle stick injury. Needle stick injuries are commonplace among healthcare workers. Needle stick injuries are defined by the United States National Institute of Occupational Safety and Health as injuries caused by needles such as hypodermic needles, blood collection needles, intravenous (IV) stylets, and needles used to connect parts of IV delivery systems. Needle stick injuries can transfer blood-borne pathogens such as Hepatitis B virus, Hepatitis C virus, and Human Immunodeficiency Virus (HIV). For healthcare workers, needle stick injuries are responsible for a significant portion of these diseases in the healthcare workforce.

It has been estimated by the Center for Disease Control, that in the United States of America, more than three million healthcare workers are exposed to blood and bodily fluids via needle stick mishaps each year. Most healthcare workers are trained with procedures for utilizing and disposing of used needles. Safety procedures dictate that used needles should not be recapped, in order to prevent the potential for needle stick injuries. However, many studies have revealed that recapping is still prevalent among healthcare workers.

In the prior art, there are many safety syringes that shield the needle before and after an injection. Such prior art safety syringes typically use an internal spring to either advance a cover over the needle or retract the needle into a cover. Such prior art patents are exemplified by U.S. Pat. No. 7,604,613 to Crawford. There are problems associated with using springs. The use of a metal spring significantly increases the costs and complexity associated with manufacturing a syringe.

Some prior art syringes use elastic elements to create a spring bias. The elastic elements are stretched when needed. However, such elastic elements are typically used to assist in advancing a plunger into a syringe and are not used to shield the needle. Such prior art syringes are exemplified by U.S. Pat. No. 5,531,696 to Menes and EP Patent No. 1,495,776 to Delgado.

A need therefore exists for an improved hypodermic needle and syringe assembly where the needle is automatically shielded using an elastic element. This need is met by the present invention as described and claimed below.

SUMMARY OF THE INVENTION

The present invention is a safety syringe system that automatically shields a needle after an injection is complete. A barrel is provided that has a first end and an opposite second end. A plunger extends into the barrel through its second end. An elastic return construct is provided that has at least one stretchable arm. The elastic return construct engages the first end of the barrel and positions each stretchable arm along the exterior of the barrel.

A sliding safety shield is provided that slides over the first end of the barrel. The sliding safety shield is positionable between a first position and a second position. In the first position, the needle is protected by the sliding safety shield. In the second position, the needle is exposed. The sliding safety shield engages and stretches the elastic return construct when moved from the first position to the second position. A locking mechanism is used to selectively lock the sliding safety shield into its second position against the bias of the elastic return construct. The plunger moves the elastic return construct forward as the plunger advances. The elastic return construct displaces the locking mechanism and releases the sliding safety shield as the plunger is fully advanced within the barrel at the end of an injection.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention needle and syringe system can be configured in many ways and can be adapted for use in many applications. However, only one exemplary embodiment is selected for the purposes of description and illustration. The illustrated embodiment, however, is merely exemplary and should not be considered a limitation when interpreting the scope of the appended claims.

Figure 1:
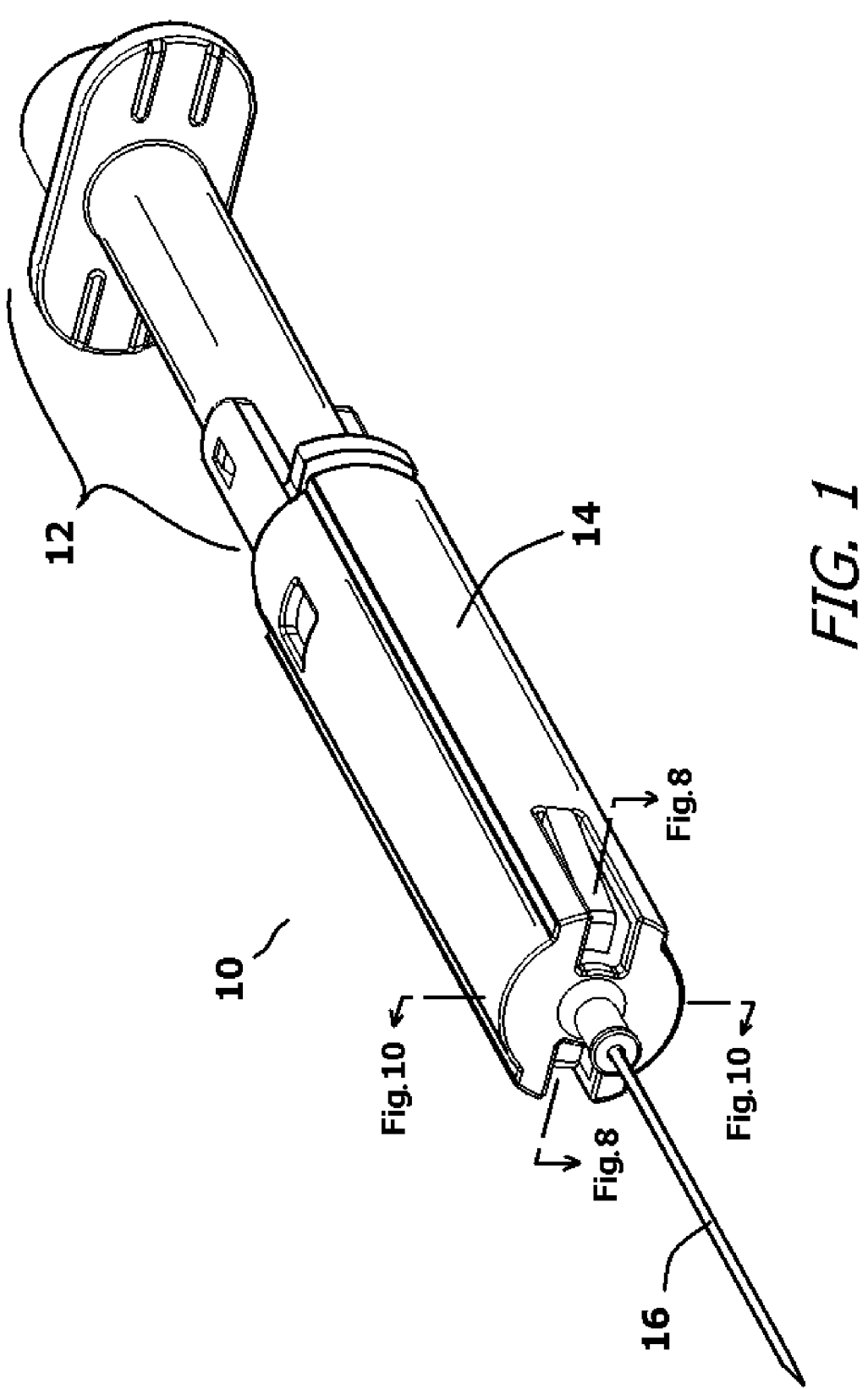
FIG. 1 is a perspective view of an exemplary embodiment of a safety needle and syringe system with a safety shield in a ready position.
Figure 2:
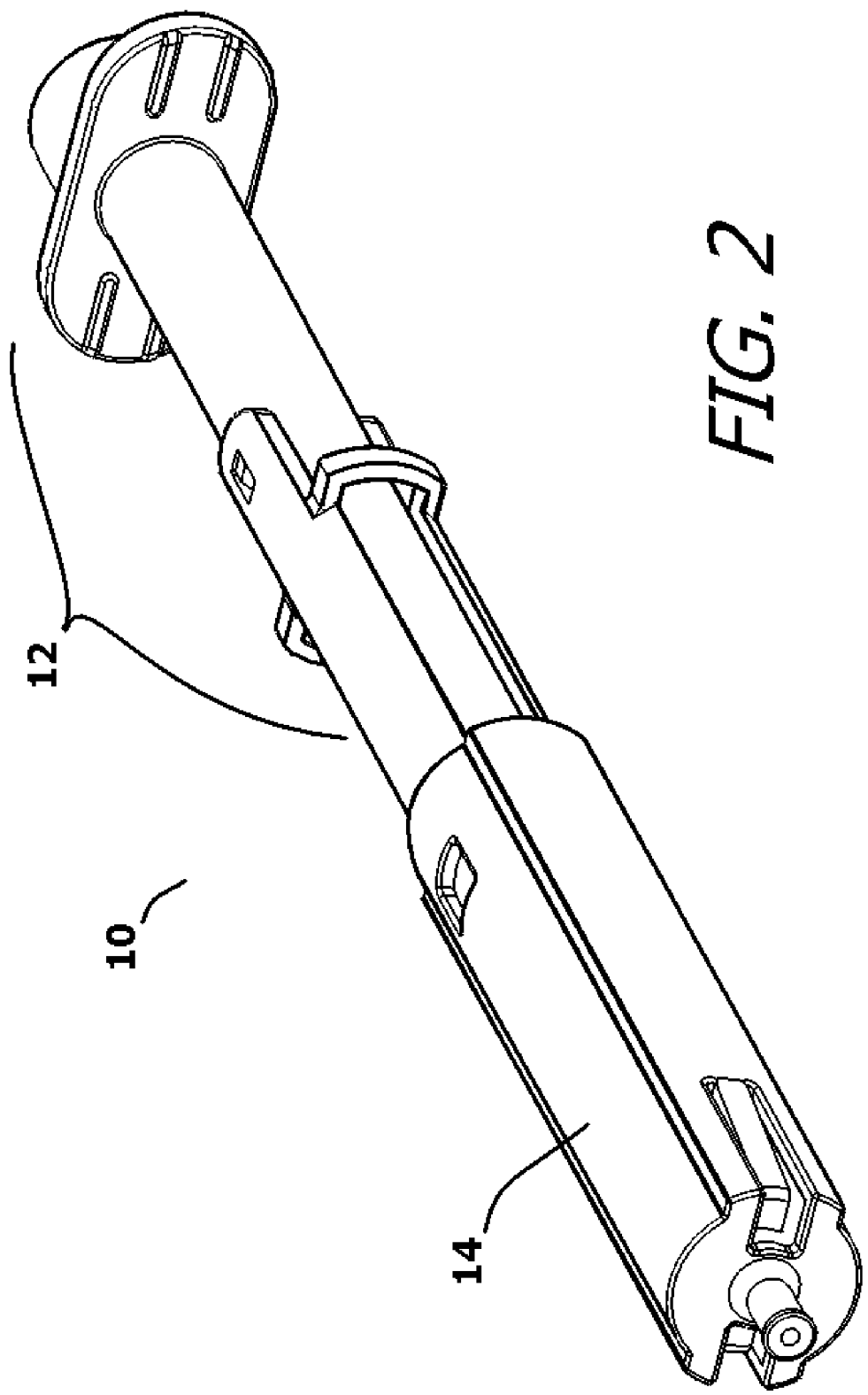
FIG. 2 is a perspective view of the exemplary embodiment of the safety needle and syringe system of FIG. 1 with a safety shield in a deployed position.

Referring to FIG. 1 in conjunction with FIG. 2, an exemplary embodiment of the present invention safety syringe system 10 is shown. In the shown embodiment, the safety syringe system 10 includes a needle and syringe assembly 12 with a sliding safety shield 14. The sliding safety shield 14 can move relative to the needle and syringe assembly 12. The safety shield 14 can move between a ready configuration (FIG. 1) and a protected configuration (FIG. 2).

The needle and syringe assembly 12 includes a needle 16. In the ready configuration (FIG. 1), the needle 16 is exposed. This enables the needle and syringe assembly 12 to be used in a traditional manner. In the protected configuration (FIG. 2), the sliding safety shield 14 covers the needle 16, therein rendering the needle 16 safe. As will be explained, the sliding safety shield 14 is biased into the protected configuration (FIG. 2). The sliding safety shield 14 covers the needle 16 prior to use of the safety syringe system 10. In the preferred embodiment, the sliding safety shield is cocked into the ready configuration before the safety syringe system 10 is packaged and shipped. However, it is also possible to sell the sliding safety shield uncocked, wherein the sliding safety shield 14 is cocked into the ready configuration just prior to use. After use, the safety syringe system 10 automatically reverts back to the protected configuration.

Figure 3:
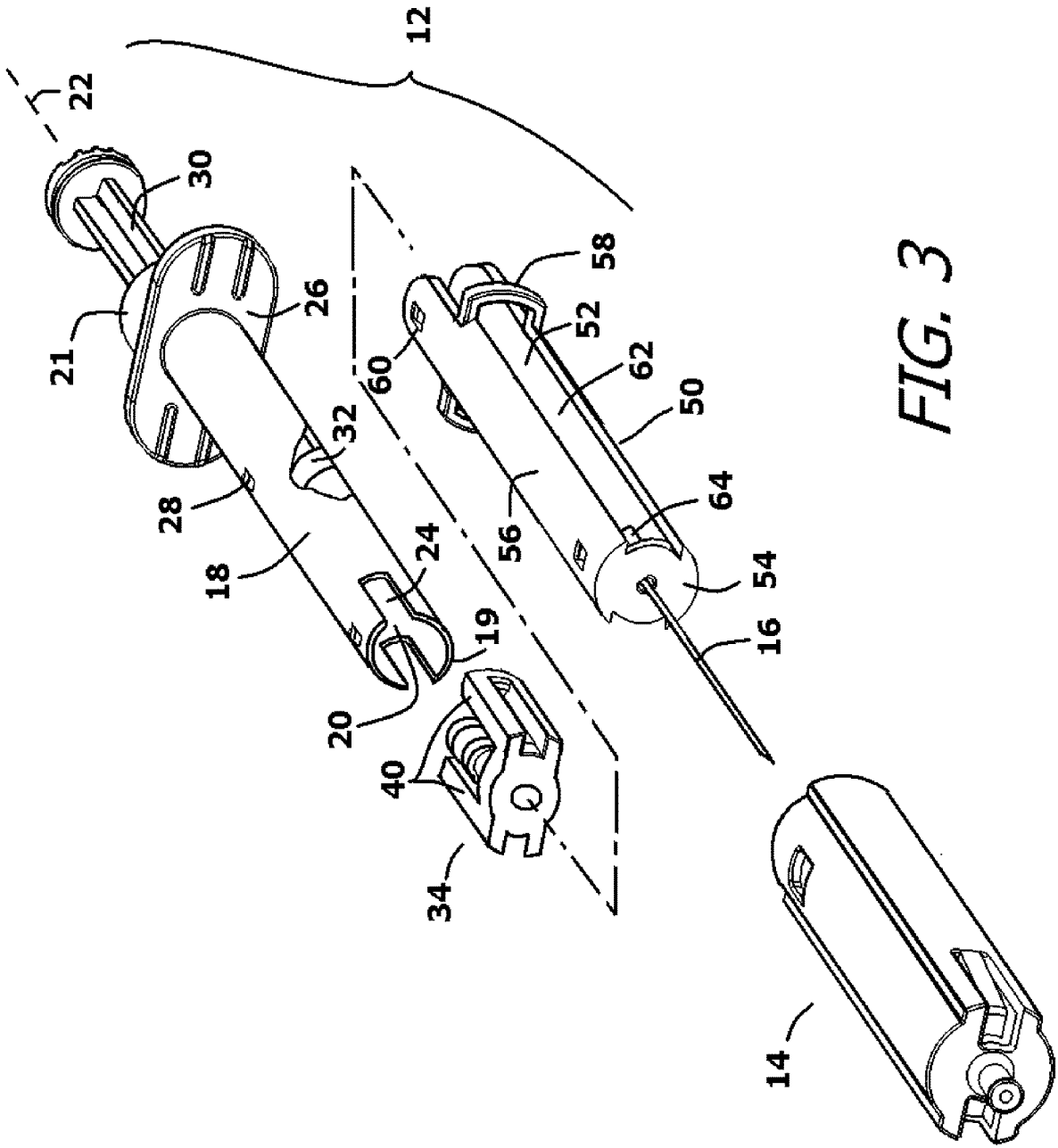
FIG. 3 is an exploded view of the exemplary embodiment of FIG. 1.

Referring to FIG. 3 in conjunction with FIG. 1 and FIG. 2, it can be seen that the needle and syringe assembly 12 includes a barrel 18. The barrel 18 is tubular and has a first end 19 and an opposite second end 21. The barrel 18 defines an open interior 20 that is symmetrically formed around a mix-axis 22 of the barrel 18. The first end 19 is slotted and contains two opposing side slots 24. The side slots 24 extend into the barrel 18 from the first end 19 for a short distance. In addition, finger flanges 26 extend from the exterior of the barrel 18 a short distance from the second end 21 of the barrel 18.

Locking tabs 28 are disposed on the exterior of the barrel 18. The locking tabs 28 are linearly aligned along lines that are parallel to the mid-axis 22 of the barrel 18. In the shown embodiment, only one set of locking tabs 28 is shown. However, it will be understood that a second set of locking tabs 28 is positioned on the opposite side of the barrel 18.

A plunger 30 is provided. The plunger 30 has a plunger head 32. The plunger head 32 is advanced into the open interior 20 of the barrel 18 through the second end 21 of the barrel 18. The plunger 30 is used to displace material through the front end 19 of the barrel 18.

Figure 4:
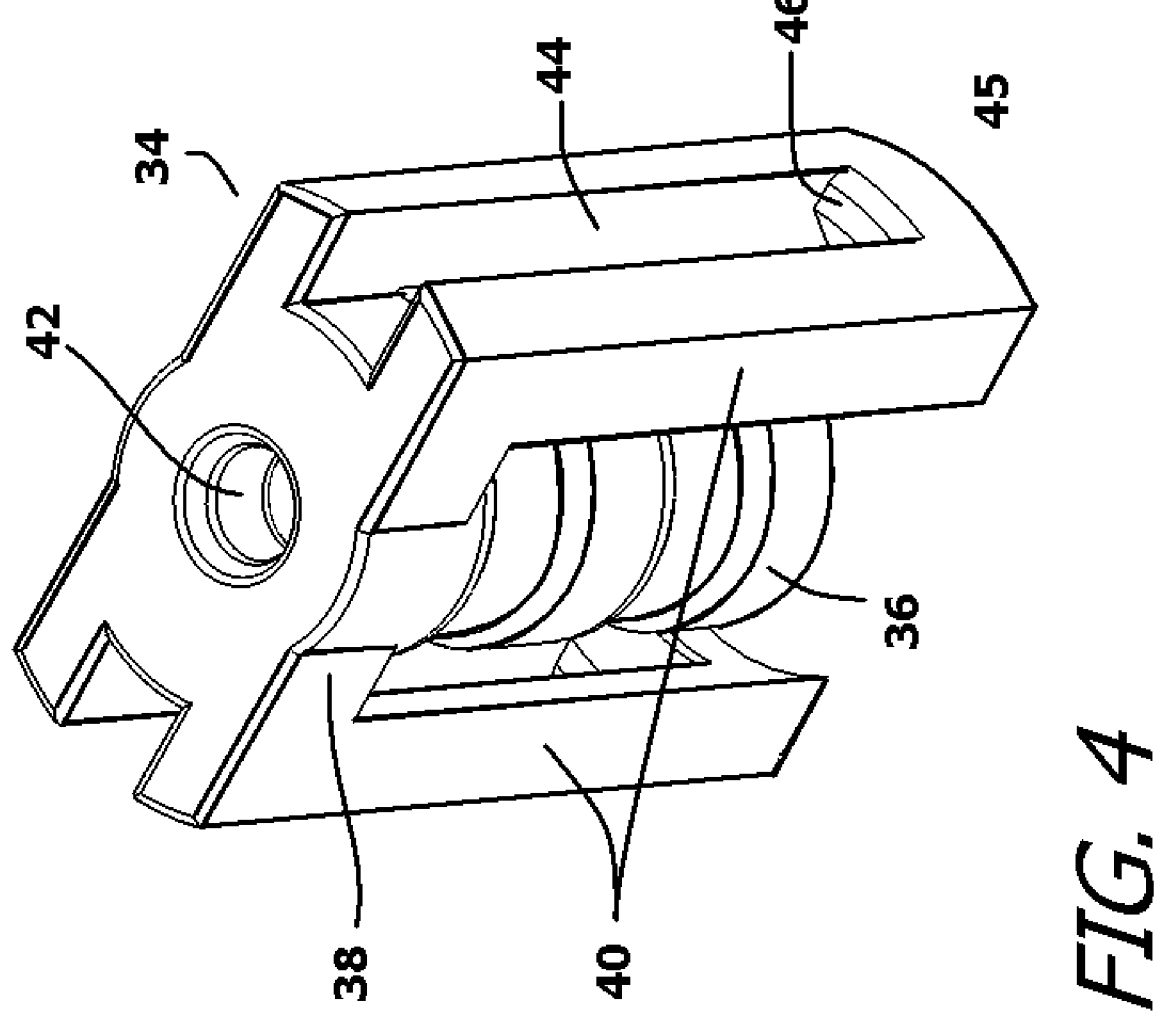
FIG. 4 is an enlarged view of the elastic construct used to create a spring bias in the safety needle and syringe system.

Referring to FIG. 4 in conjunction with FIG. 3, it can be seen that an elastic return construct 34 is provided that engages the first end 19 of the barrel 18. The elastic return construct 34 has a tubular plug 36 with an enlarged head 38 at one end. Two stretchable arms 40 extend downwardly from the enlarged head 38 on opposite sides of the tubular plug 36. The stretchable arms 40 are elastic and are capable of being elongated along the exterior of the barrel 18. As the stretchable arms 40 elongate, they store spring energy in the same manner as a rubber band.

An open conduit 42 extends through the center of the tubular plug 36 and the enlarged head 38. The tubular plug 36 is inserted into the first end 19 of the barrel 18. The enlarged head 38 passes into the two side slots 24 on the barrel 18. This enables the two stretchable arms 40 to extend along the exterior of the barrel 18 when the tubular plug 36 is inserted into the first end 19 of the barrel 18.

A groove 44 is formed in each of the stretchable arms 40. The grooves 44 extend through the enlarged head 38. However, the grooves 44 terminate prior to reaching the distal ends 45 of the stretchable arms 40. This forms a catch ledge 46 at the end of each groove 44.

Figure 5:
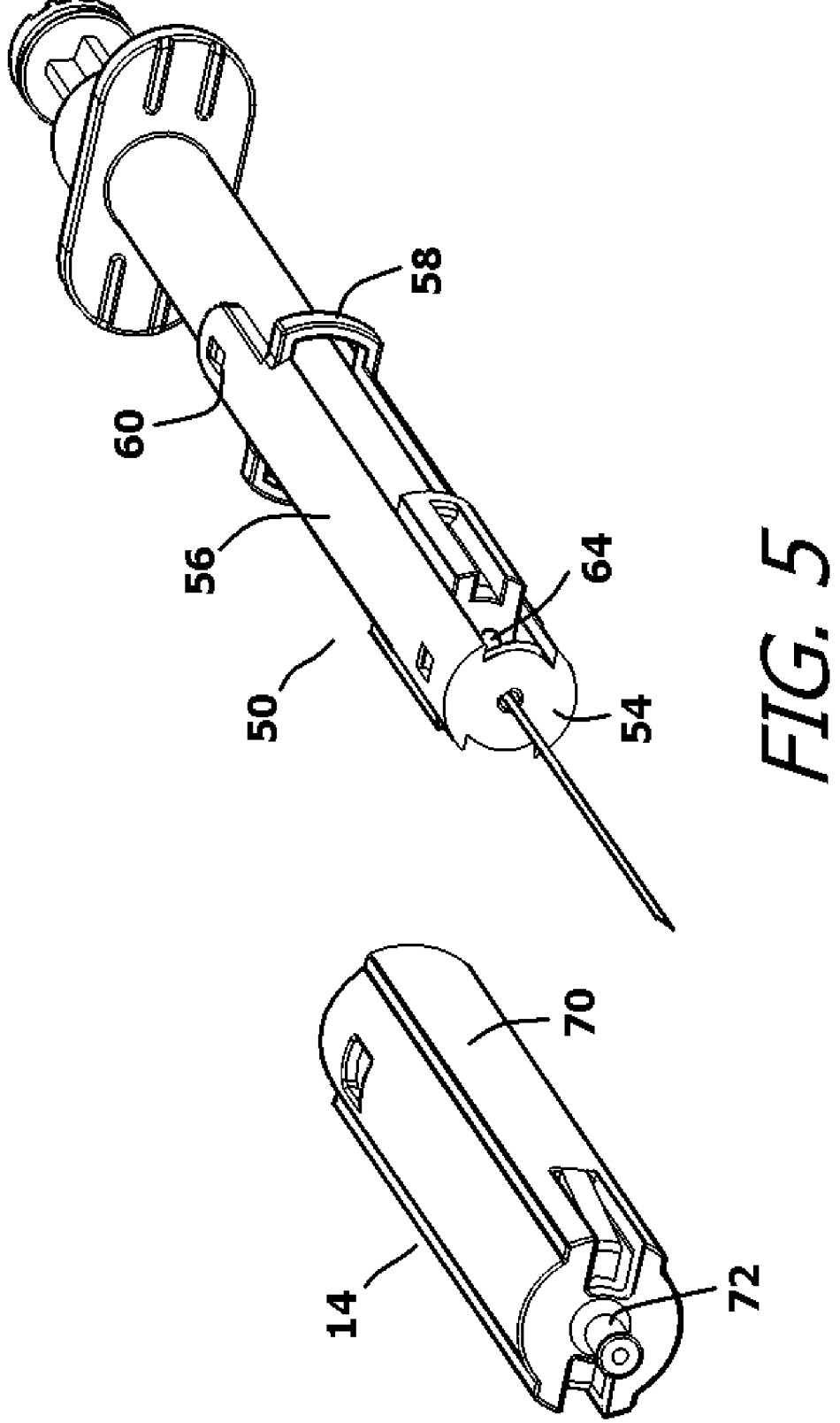
FIG. 5 is a partially exploded view of the exemplary embodiment of FIG. 1.

Referring to FIG. 5 in conjunction with FIG. 3, it can be seen that a receiving frame 50 is provided. The receiving frame 50 is a tubular structure with long side openings 52. The receiving frame 50 has an end plate 54. Two elongated sections 56 extend from the end plate 54, wherein the elongated sections 56 define opposing edges of the long side openings 52. The two elongated sections 56 are joined together by brackets 58 near the distal ends 59 of the elongated sections 56. A set of locking windows 60 are formed through each of the elongated sections 56. The receiving frame 50 is advanced over the exterior of the barrel 18 and the elastic return construct 34. The locking tabs 28 on the barrel 18 pass into the locking windows 60 on the elongated sections 56 of the receiving frame 50. This mechanically interconnects the receiving frame 50 to the barrel 18 as an assembly. Furthermore, the receiving frame 50 defines a central opening 62 that is sized to receive the first end 19 of the barrel 18 and the elastic return construct 34 that is engaged with the first end 19 of the barrel 18. When surrounding the elastic return construct 34, the stretchable arms 40 of the elastic return construct 34 extend through the long side openings 52 of the receiving frame 50.

The needle 16 extends into a needle base 64 that is part of the receiving frame 50. As such, the receiving frame 50 holds the needle 16. The needle base 64 is affixed to the end plate 54 on the receiving frame 50. The needle base 64 extends into the central opening 62. The needle 16 extends through the end plate 54 and into the needle base 64. Accordingly, the needle 16 extends from the center of the end plate 54. Furthermore, the needle 16 and the receiving frame 50 move together as an integrated assembly. The gauge of the needle 16 and the length of the needle 16 are selected by the healthcare professional for the medical procedure being performed.

Figure 6:
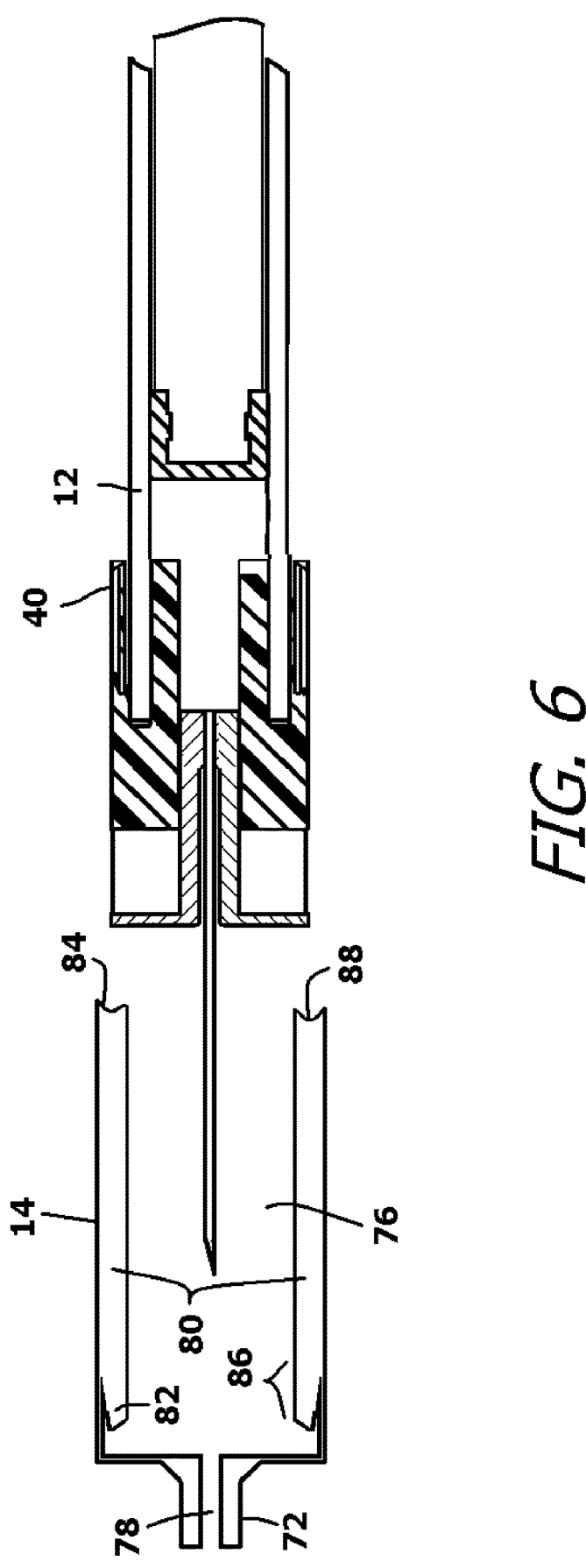
FIG. 6 is a cross-sectional view of the safety needle and syringe system as shown in FIG. 5.

The receiving frame 50 receives and retains the sliding safety shield 14 as the sliding safety shield 14 moves between its ready position and its protected position. Referring to FIG. 6 in conjunction with FIG. 5, it can be seen that the sliding safety shield 14 has a cylindrical body 70 with a needle neck 72 at one end and a frame opening 74 at the opposite end. The cylindrical body 70 defines an interior 76. A needle access hole 78 extends through the needle neck 72 and intersects the interior 76. Two ribs 80 extend inwardly into the interior 76. The two ribs 80 are opposed and are positioned to face the stretchable arms 40 of the elastic return construct 34. Each of the ribs 80 has a pawl end 82 and an opposite hook end 84. The ribs 80 are parallel until they reach a converging section approaching the pawl end 82. The converging sections create locking pawls 86. As will be later explained, each locking pawl 86 is shaped to hook and engage the end plate 54 of the receiving frame 50. Conversely, at the opposite hook end 84 of each rib 80, the rib 80 is shaped as a hook 88. As will later be explained, the hook 88 engages the catch ledge 46 in each of the stretchable arms 40.

Figure 7:
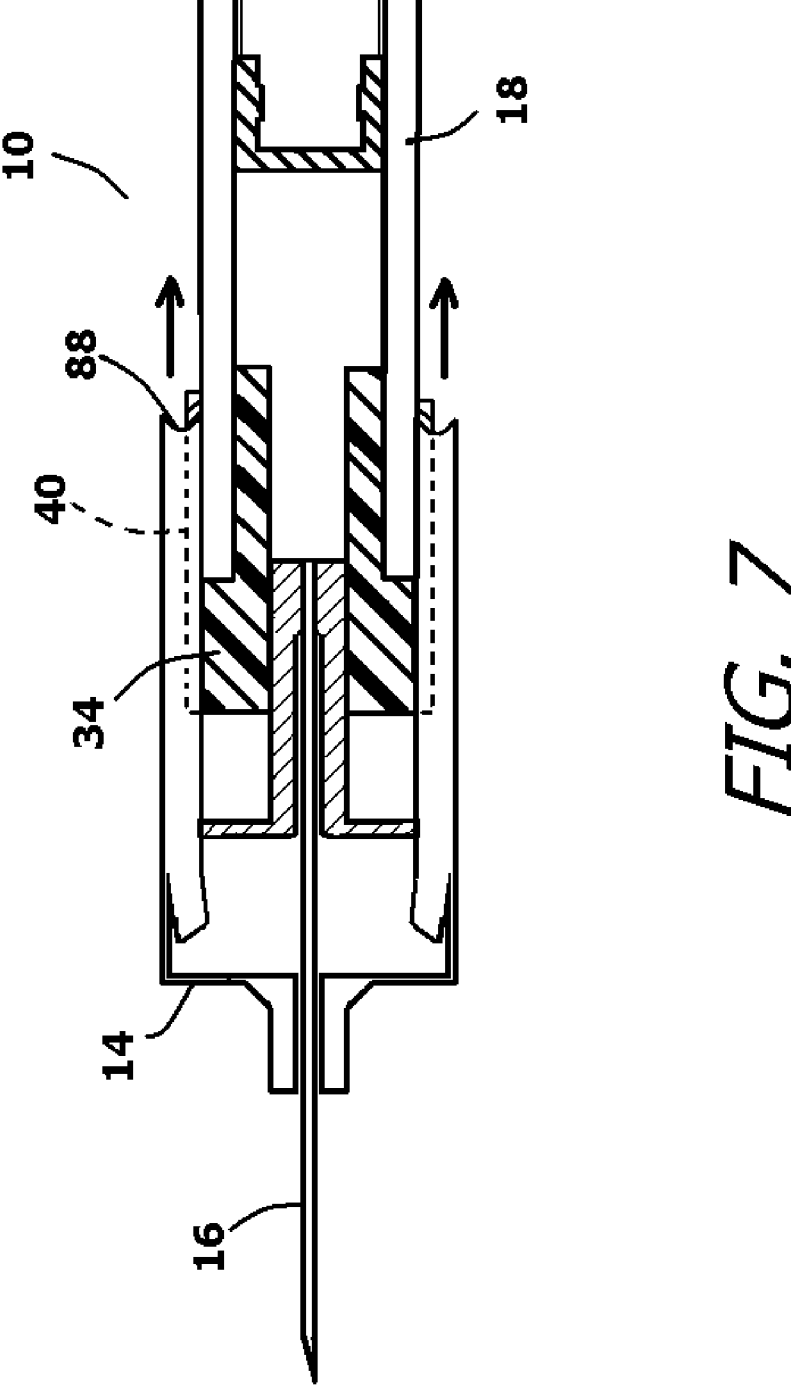
FIG. 7 is a cross-sectional view of the safety needle and syringe system shown being cocked into a ready position.

Referring to FIG. 7 in conjunction with FIG. 6, FIG. 5 and FIG. 2, it will be understood that the safety syringe system 10 can be initially packaged with the sliding safety shield 14 is advanced over the receiving frame 50 so that the needle 16 is exposed. In this configuration, the hooks 88 on the ribs 80 inside the sliding safety shield 14 engage the stretchable arms 40 of the elastic return construct 34. The stretchable arms 40 stretch and resist the further advancement of the sliding safety shield 14 toward the ready configuration. The stretchable arms 40, therefore, cause the sliding safety shield 14 to be biased into toward its protected configuration.

Figure 8:
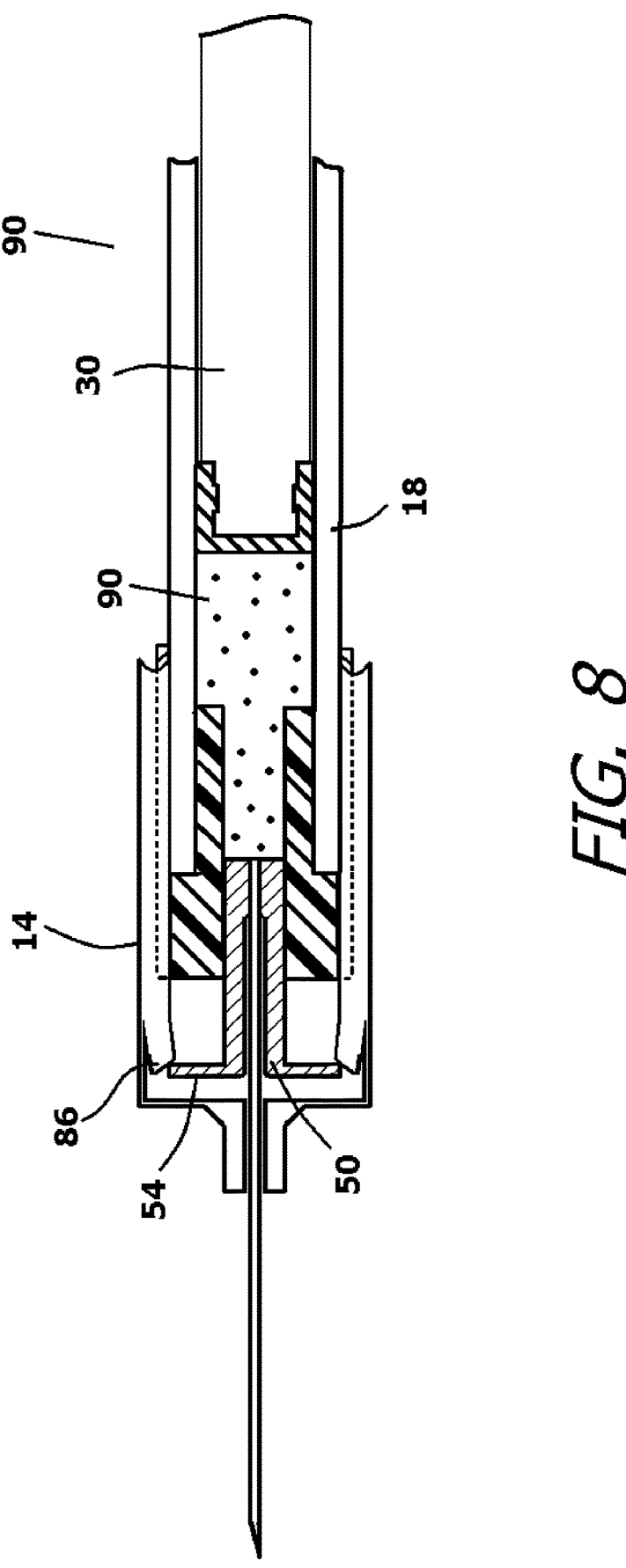
FIG. 8 is a cross-sectional view of the safety needle and syringe system of FIG. 1 shown along section line FIG. 8.

Referring to FIG. 8 in conjunction with FIG. 7, FIG. 5 and FIG. 1, it can be seen that once the sliding safety shield 14 is fully advanced onto the receiving frame 50, the locking pawls 86 inside the sliding safety shield 14 engage the end plate 54 of the receiving frame 50 and lock the safety syringe system 10 into its ready configuration. In the ready configuration, the needle 16 is exposed. The plunger 30 can then be used to draw material 90 into the barrel 18 through the needle 16 in the conventional manner.

Figure 9:
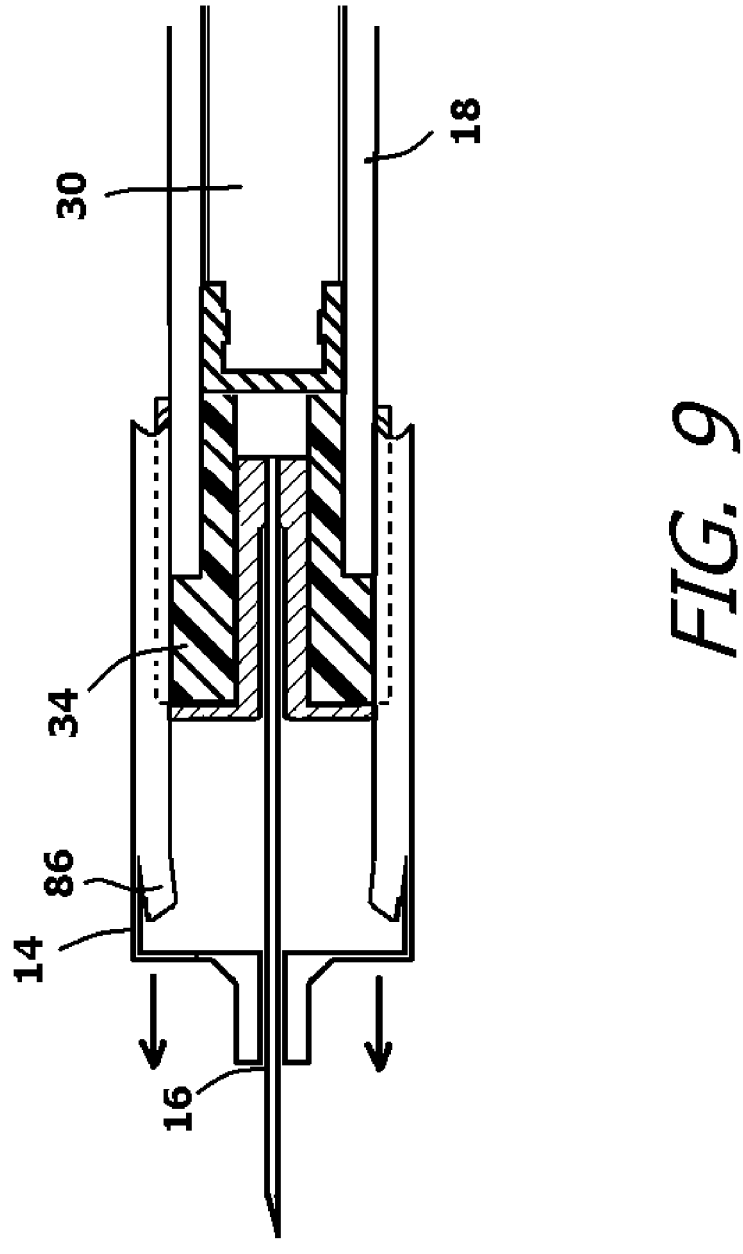
FIG. 9 is a cross-sectional view of the safety needle and syringe system shown after being triggered from a cocked position and moving toward a protected position.

Referring to FIG. 9 in conjunction with FIG. 8, it can be seen that once material 90 is drawn into the barrel 18, an injection can be made using the exposed needle 16. During the injection, the plunger 30 is advanced into the barrel 18 to displace the material 90 through the needle 16. As the plunger 30 is advanced in the barrel 18, the plunger head 32 contacts the elastic return construct 34. The elastic return construct 24 is moved by the plunger 30 as the plunger 30 is advanced. The elastic return construct 24 contacts both locking pawls 86 at the moment all the material 90 is displaced. The elastic return construct 34 spreads the locking pawls 86 and causes the locking pawls 86 to release the receiving frame 50. As such, the locking pawls 36 have two roles. The locking pawls 86 create a locking mechanism that locks the sliding safety shield 14 in a ready position Furthermore, the locking pawls 86 unlock the sliding safety shield 14 at the end of an injection. Once the locking pawls 86 release, the sliding safety shield 14 is advanced by the stretched arms 40 of the elastic return construct 34. The sliding safety shield 14 moves forward and covers the needle 16. The result is that the needle 16 is shielded, therein removing the danger of accidental contact.

Figure 10:
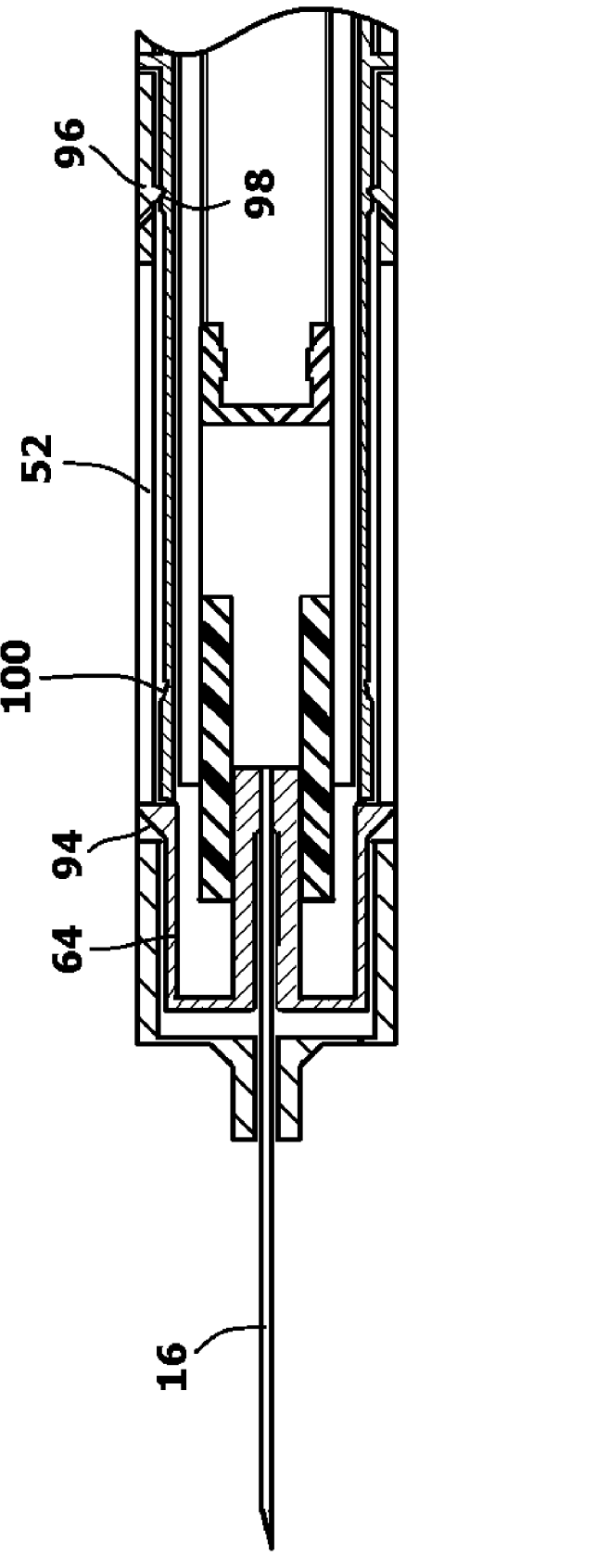
FIG. 10 is a cross-sectional view of the safety needle and syringe system of FIG. 1 shown along section line FIG. 10.

Referring to FIG. 10, it can be seen that the needle neck 64 contains stopping pawls 94 that extend into the long side openings 52 of the receiving frame 50. The stopping pawls 94 prevent the sliding safety shield 14 from moving too far forward when released. Rather, the sliding safety shield 14 is stopped at the proper position to cover the needle 16.

Additionally, locking pawls 96 are formed in the cylindrical body 70 that engage the receiving frame 50. Two sets of reliefs 98, 100 are formed in the receiving frame 50 to engage the locking pawls 96. When the sliding safety shield 14 is cocked for the first time, the locking pawls 96 engage the first set of reliefs 98. Once released, the locking pawls 96 index to the second set of reliefs 100. This prevents the sliding safety shield 14 from being re-cocked and reused.

It will be understood that the embodiment of the present invention that is illustrated and described is merely exemplary and that a person skilled in the art can make many variations to that embodiment. All such embodiments are intended to be included within the scope of the present invention as defined by the appended claims.

What is claimed is:

1. A safety syringe system, comprising:
a barrel having a first end and an opposite second end;
a plunger extending into said barrel through said second end;
an elastic return element having a tubular plug and at least one arm, wherein said tubular plug extends into said first end of said barrel and said at least one arm extends outside of said barrel toward said second end of said barrel;
a sliding safety shield that slides between a first position and a second position relative to said barrel, wherein said sliding safety shield engages said at least one arm and stretch said at least one arm toward said second end of said barrel when said sliding safety shield is moved from said first position to said second position, wherein said at least one arm stretches and biases said sliding safety shield into said first position.

2. The system according to claim 1, further including a needle, wherein said sliding safety shield protects said needle when in said first position.

3. The system according to claim 2, further including a locking mechanism for selectively locking said sliding safety shield into said second position.

4. The system according to claim 3, wherein said plunger moves to unlock said locking mechanism when said plunger is advanced in said barrel.

5. The system according to claim 1, further including a receiving frame that passes over a part of said barrel, wherein said sliding safety shield slides along said receiving frame between said first position and said second position.

6. The system according to claim 5, wherein said receiving frame is affixed to said barrel.

7. The system according to claim 6, wherein a needle is affixed to said receiving frame.

8. The system according to claim 7, wherein said sliding safety shield protects said needle when in said first position.

9. The system according to claim 5, wherein said sliding safety shield contains internal pawls that engage said receiving frame and hold said sliding safety shield in said second position.

10. The system according to claim 9, wherein said plunger displaces said elastic return element, wherein said elastic return element disengages said internal pawls from said receiving frame as said plunger is fully advanced into said barrel.

11. A safety syringe system, comprising:
a barrel having a first end and an opposite second end;
a plunger extending into said barrel through said second end;
an elastic return element having a plug that extends into said first end of said barrel and arms that extend along said barrel toward said second end of said barrel;
a needle;
a sliding safety shield that slides between a first position and a second position, wherein said sliding safety shield stretches said arms of said elastic return element toward said second end of said barrel when said sliding safety shield is moved from said first position to said second position, and wherein said sliding safety shield protects said needle in said first position.

12. The system according to claim 11, further including a locking mechanism for selectively locking said sliding safety shield into said second position.

13. The system according to claim 12, wherein said plunger moves to unlock said locking mechanism when said plunger is advanced in said barrel.

14. The system according to claim 11, further including a receiving frame that passes over a part of said barrel, wherein said sliding safety shield slides along said receiving frame between said first position and said second position.

15. The system according to claim 14, wherein said receiving frame is affixed to said barrel.

16. The system according to claim 14, wherein said sliding safety shield contains internal pawls that engage said receiving frame and hold said sliding safety shield in said second position.

17. The system according to claim 16, wherein said plunger disengages said internal pawls from said receiving frame as said plunger is fully advanced into said barrel.

18. A safety syringe system, comprising:

a barrel having a first end and an opposite second end;

a plunger extending into said barrel through said second end;

a needle;

elastic arms that extend outside of said barrel from said first end of said barrel toward said second end of said barrel;

a sliding safety shield positionable between a first position that covers said needle and a second position that exposes said needle, wherein said sliding safety shield stretch and elongate said elastic arms when said sliding safety shield is moved from said first position to said second position, wherein said elastic arms bias said sliding safety shield toward said first position.

19. The system according to claim 18, further including a locking mechanism for selectively locking said sliding safety shield into said second position.

20. The system according to claim 19, wherein said plunger moves said elastic return construct to unlock said locking mechanism when said plunger is advanced in said barrel.

* * * * *